United States Patent [19]

Novotny et al.

[11] Patent Number: 5,292,416
[45] Date of Patent: Mar. 8, 1994

[54] PULSED-FIELD SEPARATION OF POLYSACCHARIDES IN CAPILLARIES

[75] Inventors: Milos V. Novotny; Jan Sudor, both of Bloomington, Ind.

[73] Assignee: Indiana University Foundation, Bloomington, Ind.

[21] Appl. No.: 975,314

[22] Filed: Nov. 13, 1992

[51] Int. Cl.$^5$ ............................................. C25B 7/00
[52] U.S. Cl. ................................. 204/182.8; 536/127
[58] Field of Search .................... 204/182.8; 536/127

[56] References Cited
U.S. PATENT DOCUMENTS 5,122,248 6/1992 Karger et al. ................... 204/182.8

OTHER PUBLICATIONS

CA 113(20):184004k, "Indirect Fluorescence detection of sugars separated by capillary zone electrophoresis with visible laser excitation".
CA 115(1):4532r, Ultrasensitive fluorometric detection of carbohydrates as derivatives in mixtures separated by capillary electrophoresis.

Primary Examiner—John Niebling
Assistant Examiner—C. Delacroix
Attorney, Agent, or Firm—Townsend and Townsend Khourie and Crew

[57] ABSTRACT

Polysaccharides are separated in a capillary using pulsed-field electrophoresis.

20 Claims, 5 Drawing Sheets

PULSED-FIELD SEPARATION OF POLYSACCHARIDES IN CAPILLARIES

This invention resides in the fields of capillary electrophoresis and alternating-field electrophoresis. This invention resides in part in a unique convergence of these two fields in a manner producing unusual and unexpected results.

BACKGROUND OF THE INVENTION

Early studies leading to the development of high-performance capillary electrophoresis (HPCE) were those of Jorgenson and Lukacs. Jorgenson, J. W., et al., Anal. Chem. 53:1298 (1981); Jorgenson, J. W., et al., Clin. Chem. 27:1551 (1981); Jorgenson, J. W., et al., J. Chromatogr. 218:209 (1981). The experiments reported in these studies demonstrated that extremely high efficiencies in the separation of ionic molecules can be achieved in a narrow-bore capillary, i.e., one of less than 100 microns inner diameter, by applying a high, constant voltage between the two ends of the capillary, thereby causing the molecules to migrate toward one of the electrodes in discrete zones according to molecular weight, and permitting detection of the zones by focusing a sufficiently sensitive detector on a point in the migration path. The basic experimental arrangement of Jorgenson, et al. has since been used in the separation of various types of molecules, both small and large, in a highly efficient manner. In some systems, the electrophoretic principle serves as the basis for these separations. In others, the separations are the result of electroosmotic action in micellar or other buffer-modified systems. See, Tsuda, T., et al, J. Chromatogr. 264:385 (1983); Terabe, S. et al., Anal. Chem. 56:111 (1984); Terabe, S., et al., Anal. Chem. 57:834 (1985); and Foley, J. P., Anal. Chem. 62:1302 (1990). Still other systems rely on the electroosmotic action on microemulsions. Watarai, H., Chem. Lett. (Japan) 391 (1991). Application of the method to highly charged polymers, such as oligo- and polynucleotides, was demonstrated by Cohen, A. S., et al., Proc. Natl. Acad. Sci. U.S.A. 85:9660 (1988), who report the separation of such polymers in chemically immobilized gels such as crosslinked polyacrylamides. Because of these and additional developments, HPCE is now a highly successful and widely commercialized instrumental analytical method.

The choice of separation medium to be used inside a capillary in HPCE is often fundamental to the success of a given separation problem. As a result, many investigators have discovered that by careful selection and modification of the separation medium one can achieve separations of components which are otherwise difficult to separate. This has led, for example, to the use of cyclodextrins, micellar systems and chiral gels for the separations of chiral entities. Fanali, S., J. Chromatogr. 474:441 (1989); Liu, J. et al., J. Chromatogr. 519:189 (1990); Terabe, S., et al. J. Chromatogr. 516:23 (1990); Guttman, A. et al., J. Chromatogr. 448:41 (1988). Other examples are the separations of proteins in surface-coated open tubes. Hjertén, S., J. Chromatogr. 347:1991 (1985); Cobb, K. A., et al., Anal. Chem. 62:2478 (1990); Wiktorowicz, J. E., et al, Electrophoresis 11:769 (1990); Town, J. K., et al., J. Chromatogr. 516:69 (1990). Still further examples are the separation of oligosaccharides in highly concentrated, immobilized gels. Liu, J., et al., J. Chromatogr. 559:223 (1991).

Nevertheless, large biopolymers, such as polysaccharides, certain proteins, or fragments of nucleic acids, do not respond well to attempts at capillary electrophoresis, either in open tubes filled with buffer solution or in tubes containing immobilized gels. In buffer-filled open tubes, large biopolymers tend to migrate together. In gel-filled capillaries, the pore structures of the gels are resistant to penetration by very large molecules, thereby interfering with the successful movement of the molecules past the detector. On the other hand, successful separations have been achieved in some cases by using separation media consisting of viscous solutions of polymers, such as water-soluble derivatives of cellulose, low-melting agarose, galactomannan, linear polyacrylamides, polyethylene glycols, and polyvinyl alcohols. Zhu, M. D., et al., U.S. Pat. No. 5,089,111 (Feb. 18, 1992); Grossman, P. D., et al., Biopolymers 31:1221 (1991). The polymeric solutes in these solutions form networks of aggregates which are sufficiently flexible to yield to the large polyionic species sought to be separated as these species migrate under the influence of an electric field.

A property of very large biopolymers such as chromosomal DNA is their tendency to stretch in an electric field, exhibiting what is known in the literature as "reptation." De Gennes, P. G., et al., Scaling Concepts in Polymer Physics, Cornell University Press, Ithaca, N.Y. (1979); Lerman, L. S., et al., Biopolymers 21:995 (1982); Lumpkin, O. J., et al., Biopolymers 24:1573 (1985). Reptation causes molecules of vastly different chain lengths to migrate through the separation medium network at very similar speeds, spoiling the attempt at separation. This phenomenon was recognized and turned to advantage by Schwartz, D. C., et al., Cell 37:67 (1984), who designed an experiment in which these large molecules were subjected to alternating fields at an angle relative to each other and to the direction of migration. During the alternating, or "pulsing," of the fields in this manner, the molecular distortions in the form of shape reorientations and the formation of kinks or "hernias" which occur during reptation alternate with molecular relaxation, and the rates at which the distortion and relaxation occur vary with the sizes of the molecules in question. These differing rates of response within each portion of the alternation cycle result in differing rates of the overall or averaged migration for each species, which in turn results in a separation of the species on the basis of their molecular weight.

In the various studies which have since been reported, the alternations in the electric field have been performed by switching between fields oriented at angles relative to each other, as well as between fields which are rotated a full 180° relative to each other, the latter commonly referred to as "field inversion." Like the studies using angled fields, studies involving field inversion have largely been performed in slab-shaped media, and most such studies have involved the separation of molecules of the size of very large DNA chains, i.e., approximately $10^5$ to $10^7$ bases in size ($10^7$ to $10^9$ daltons). Little or no effect has been observed in attempts to separate smaller molecules by these techniques. The separation medium most widely used has been low-melting agarose. Schwartz, D. C., et al., Cell 37:67 (1984); Carle, G. F., et al., Science 232:65 (1986). Fields strengths most commonly used are within the range of 2 to 10 V/cm, with separations taking hours, and even days.

An attempt at the use of field inversion (or "pulsed fields") in capillaries is reported by Heiger, D. N., et al., *J. Chromatogr.* 516:33 (1990). The major portion of the experimental results reported by these authors was obtained using continuous (nonalternating) fields rather than pulsed fields, however, and the only attempts at pulsed-field separations involved a mixture of only two double-stranded DNA fragments, each of which had a molecular weight well in excess of 2,000,000, and for which the authors had already exhibited complete resolution in a continuous-field experiment. In two of the pulsed-field experiments, the peak separation was no greater than that achieved in the continuous-field experiment. An increase in peak separation was achieved when the pulsing frequency was varied, but the maximum improvement over a total of eight attempts was only a 25% increase in the separation. Other than this, no successful application of the pulsed-field technique to HPCE has been reported. This may have been due to experimental difficulties involved in pulsing at the high voltages normally used in HPCE (typically 100 to 300 V/cm), the perceived importance of pulsing angles other than 180° C., or difficulties in the selection of such parameters as appropriate column matrices and sample concentrations.

It is for these reasons that the present invention is surprising and unexpected in view of the state of the art.

SUMMARY OF THE INVENTION

It has now been discovered that carbohydrates, and particularly polysaccharides, can be effectively and efficiently separated by field inversion electrophoretic pulsing in capillary tubes. What makes this discovery surprising is that mixtures of carbohydrates which do not separate in capillaries under the influence of a continuous electrophoretic field, do indeed separate under alternating field inversion conditions. Furthermore, the technique is useful in separating carbohydrates of molecular weights considerably lower than those of the DNA fragments for which the pulsed field techniques of the prior art are best known. Still further, the technique involves a unique extension of pulsed-field technology into systems where the field strength is considerably greater than field strengths which have heretofore been used with pulsed fields.

Further objects, advantages, and features of the present invention will become apparent from the description which follows.

DETAILED DESCRIPTION OF THE INVENTION AND PREFERRED EMBODIMENTS

The separations of the present invention are performed in capillaries which may vary widely in length, diameter, material of construction and orientation. In most applications, however, the capillary will have an inner diameter ranging from about 5 microns to about 300 microns, preferably from about 20 microns to about 100 microns, and a length ranging from about 10 cm to about 3,000 cm, preferably from about 20 cm to about 100 cm. Depending on the location of the detector, the effective length, which is the length which the solute zones must travel before they reach the detector, may be somewhat less.

The capillary may be constructed of a wide range of materials, limited only by the requirements that it be chemically inert and electrically non-conducting. While chemical inertness and electrical non-conductivity may be imparted to the capillary by surface coatings, it is preferred for purposes of convenience, safety and longevity over repeated uses that the capillary itself have these qualities, particularly since the coatings are applied for other, distinct purposes. With these considerations in mind, the capillary may be constructed, for example, of glass or other silica-containing materials, of plastics, or of metals such as stainless steel. Transparent materials are preferred, both for purposes of on-line detection and for purposes of monitoring the capillary interior as it is being filled with the separation medium and during the electrophoresis itself. Capillaries of quartz and fused silica are particularly convenient and useful.

While a wide variety of separation media may be used in the capillary, this invention is of particular utility when the separation medium is a polymer matrix. Examples include polymers which are not crosslinked as well as those which are. Noncrosslinked polymers include linear polyacrylamide, polyethylene oxide, and polycarbohydrates such as modified cellulose derivatives and galactomannan. A prominent example of a crosslinked polymer is crosslinked polyacrylamide. The concentration of the gel and methods of filling the capillary with the gel are known among those skilled in the art and well documented in the literature. See, for example, *Capillary Electrophoresis, Theory and Practice*, Grossman, P. D., et al., eds., Academic Press, Inc., San Diego, Calif. (1992).

The imposition of an electric potential between the two ends of the capillary is likewise achieved by conventional means. The field pulsing will consist of intervals of a positive field strength in the forward direction, i.e., the direction of migration of the sample components from the injection end of the capillary into the capillary towards the detection point, separated by intervening intervals of either a zero field strength or of a field strength in the reverse direction. The separations will generally be performed using field strengths (i.e., voltage gradients) of about 10 V/cm or higher, where non-zero field strengths are used. In preferred embodiments, the field strengths range from about 30 V/cm to about 3,000 V/cm, and in most preferred embodiments, from about 100 V/cm to about 1,000 V/cm.

The switching protocol may vary widely, but will be selected in each case both to result in an overall migration of the components of the sample mixture through the capillary in the forward direction and to provide the optimum separation of the components into discrete zones on the basis of their molecular weights. To achieve these results, the parameters which may be varied include whether or not a reverse field is applied in the intervening intervals, whether the same field strength or different field strengths are applied in both the forward and reverse fields, the magnitudes of the field strengths, the durations of the intervals, and the ratios of the durations of the forward field intervals to the intervening intervals.

In preferred embodiments of the invention, the protocol includes a reverse field rather than a zero field during the intervening intervals. The forward field time intervals and the intervening or reverse field time intervals may either be of constant duration or of varying duration, such as continuously increasing duration. In preferred methods, however, the forward field time intervals are of equal duration and the intervening or reverse field time intervals are also of equal duration. Furthermore, the net effect of the ratio of forward field strength and time to the intervening or reverse field strength and time should be such that the overall migration is positive. Thus, the duration of the forward field time intervals should exceed the duration of the intervening or reverse field time intervals in cases where the field strength of the intervening or reverse field is equal to or greater than the field strength of the forward field. In cases where the field strength of the forward field is greater than the field strength of the intervening or reverse field, the duration of the intervening or reverse field may be equal to or even greater than the duration of the forward field.

In preferred embodiments of the invention, the forward field intervals alternate with the intervening intervals at a frequency of from about 0.03 Hz to about 300 Hz, most preferably from about 0.1 Hz to about 100 Hz.

This invention is applicable to the separation of polycarbohydrates of a wide range of molecular weights. The invention is particularly useful in the separation of polysaccharides ranging in molecular weight from as low as 1,000 to as high as 100,000,000, preferably from about 3,000 to about 2,000,000, and most preferably from about 5,000 to about 500,000.

The polycarbohydrate mixture to be separated will generally be applied to the capillary in the form of a liquid solution. Loading of a sample of the solution into the capillary is accomplished by conventional means, generally involving introducing the sample a short distance into one end of the capillary. A prominent and particularly convenient method for doing this uses the electrophoretic principle, using the same electric equipment used during the electrophoretic separation but with a continuous electric field of limited duration, such as ten to twenty seconds, at a low voltage.

Response of the polysaccharides to the electric field occurs as a result a charged moieties in the molecular structure of the polysaccharides. Some polysaccharides, such as hyaluronic acids, chondroitin sulfate and heparin-like molecules, possess native charged moieties. For those which do not, the hydroxy groups of the sugar residues can serve as sites for an equilibrium-based attachment of charged moieties. One method of achieving this attachment is by the inclusion of borate ion in the buffer medium. Other charged species and the associated chemical interactions with analogous results will be apparent to those skilled in the art.

Detection of the separated solute zones may be achieved in a variety of ways known to those skilled in the art. Examples are fluorescence, UV light absorbance, thermooptical detection, mass spectrometry detectors, amperometric detectors, conductivity detectors, radiometric detectors, Raman-based detectors, and refractive-index detectors. Many of these methods may be applied either on-line (directly through the capillary tube) or on the solutes as they pass out of the capillary. The apparatus and experimental arrangement for such detection methods are well known in the art of capillary electrophoresis. On-line detection is preferred.

For fluorescence-based detection methods, the polysaccharides are labeled with a suitable fluorophore. For neutral polysaccharides with a reducing end, this may be accomplished by reductively aminating the aldehydic group, then attaching a fluorescent label. Examples of fluorescent labels which can be attached in this manner are orthophthalaldehyde (OPA), fluorescamine, and 3-(4-carboxybenzoyl)-2-quinolinecarboxaldehyde (CBQCA). Aminopolysaccharides such as chitosan can be tagged directly with these agents. In an alternate method, tagging reagents which themselves contain an amino group and are capable of forming a Schiff base with neutral sugars can be employed without reductive amination.

For the remainder of the electrophoretic system, conventional components known to those skilled in the art may be used. These include the buffers, the electrodes and the power supply. The electrodes are preferably driven by a power supply and field switching unit designed for pulsed-field electrophoresis. Among the various commercially available units are the Model 3000xi Electrophoresis Power Supply. in combination with a modified Pulsewave 760 Electrophoretic Field Switcher capable of switching 3,000 V, all available from Bio-Rad Laboratories, Inc., Hercules, Calif., USA. Alternatively, the electrodes can be driven by a switching power supply such as units obtainable from Trek, Inc., Medina, N.Y., USA.

The following examples are offered for purposes of illustration, and are intended neither to limit nor to define the invention in any manner.

The experiments reported in these examples were conducted in fused silica capillaries of 50-micron inner diameter, 187-micron outer diameter, and of different lengths as specified in the examples themselves. The inner surfaces of the capillaries were coated with linear polyacrylamide and the outer surfaces were coated with polyamide. For each experiment, the capillary was enclosed in a clear plastic box designed for electrical safety, and power was supplied by a high-voltage dc power supply capable of delivering 0-30 kV (Spellman High Voltage Electronics, Plainview, N.Y. USA). Periodic field inversion was achieved by a 10 kV operational amplifier (Model 10/10, supplied by Trek, Inc., Medina, N.Y., USA) controlled by a function generator (Beckman Industrial Corporation, Emerson Electric Co., Brea, Calif., USA).

On-column fluorescence measurements were performed with an argon-ion laser (Omichrom, supplied by Chino, Calif., USA) as a light source, supplying 5 mW power at 457 nm, through a short section of the fused silica capillary from which the polyimide coating had been removed. Fluorescence emission was collected at 555 nm through a 600-micron fiber optic placed at a right angle to the incident laser beam. Signals isolated by a band-pass filter were monitored with a R928 photomultiplier tube and amplified with a Model 128A lock-in amplifier (EG&G Princeton Applied Research, Princeton, N.J., USA).

Dextran standards of molecular weights of 8,800, 39,100, 70,000, 503,000, and 2,000,000, were purchased from Sigma Chemical Company, St. Louis, Mo., USA, and further dextrans of molecular weights of 48,600 and 667,800 were purchased from Fluka Chemical Corp., Ronkonkoma, N.Y., USA. The compound 3-(4-carboxybenzoyl)-2-quinolinecarboxaldehyde (CBQCA), synthesized by known techniques, was used as a fluorogenic reagent. The acrylamide, ammonium persulphate, sodium borate, boric acid, sodium phosphate, ammonium chloride, and tris((hydroxymethyl)aminomethane) used were analytical grade reagents from Sigma Chemical Company. The sodium cyanborohydride was a product of Aldrich Chemical Company, Inc., Milwaukee, Wis., USA. The potassium cyanide was purchased from Mallinkrodt, Inc., St. Louis, Mo., USA. The carboxymethylcellulose was obtained from Astra Hassle (Sweden), and the cellulose, EC 3.2.1.4, from *Trichoderma viride*, was purchased from Sigma Chemical Company.

EXAMPLE 1

This example is a study of continuous-field (i.e., constant-field) capillary electrophoresis on a mixture of oligosaccharides. This example is included for comparative purposes and does not employ the method of the present invention.

A mixture of oligosaccharides was prepared by enzymatic cleavage of the carboxymethylcellulose with a cellulose: substrate weight ratio of 1:100, in 100 mM sodium phosphate buffer at pH 5.0 and 37° C. The enzymatic reaction was stopped after one hour by heating the mixture for ten minutes at 100° C., followed by removal of the enzyme by passing the entire digest through a C-18 cartridge (Millipore Corporation, Bedford, Mass., USA). This was followed by reductive amination of the remaining sample to attach the fluorescence label. The sample was then desalted by microdialysis on a Millipore MF Membrane (0.025 micron pore size (Millipore Corporation).

Electrophoresis was conducted in a capillary of 30 cm effective length (45 cm total length), filled with 18% Instacryl (International Biotechnologies, Inc., New Haven, Conn.) solution. The buffer used was 25 mM boric acid/25 mM sodium phosphate/50 mM Tris (pH 9.1). Loading of the sample was achieved by electromigration injection for ten seconds at 2 kV. Electrophoresis was conducted under an applied voltage of 15 kV (4 µA).

Figure 1:
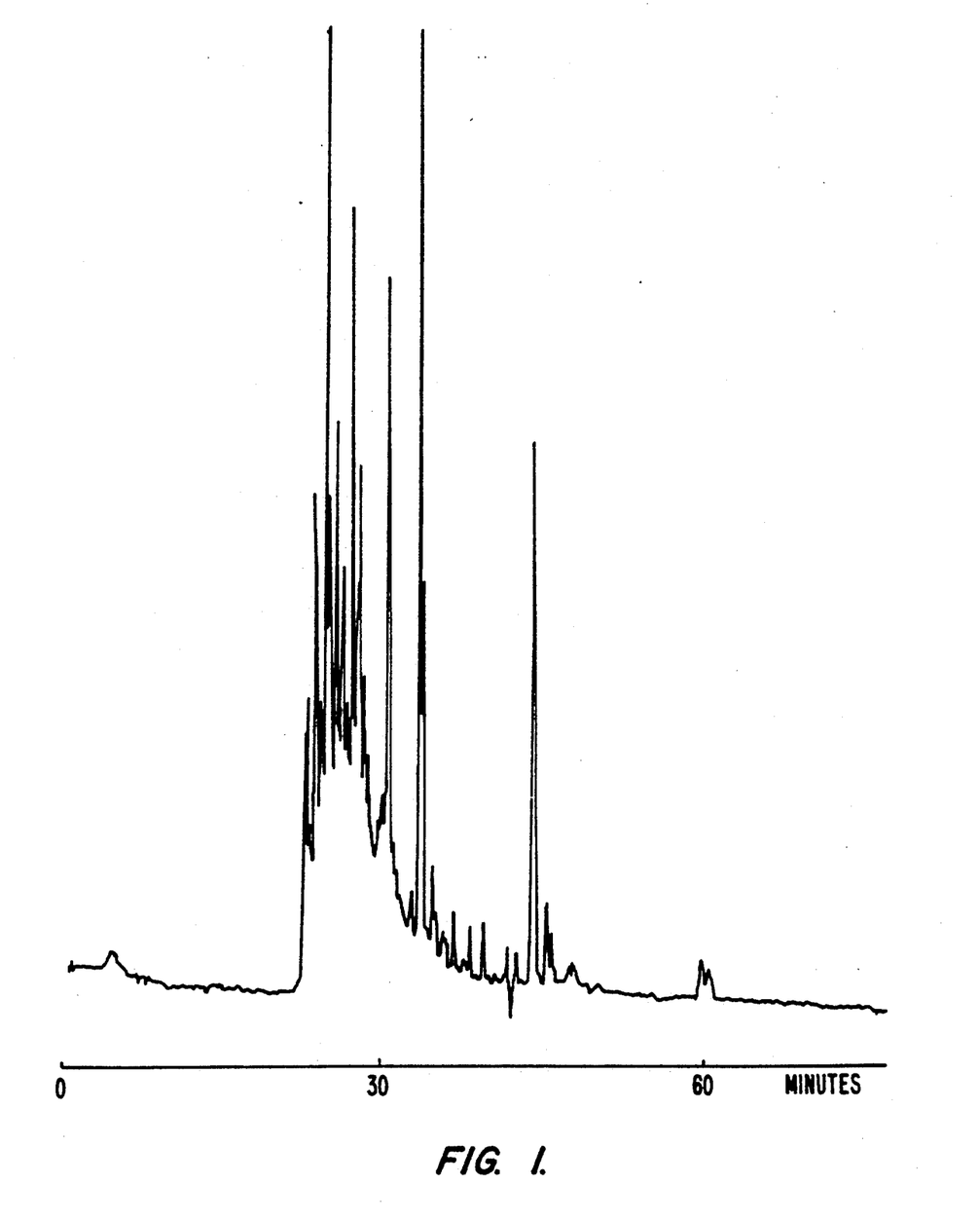
FIG. 1 is a detector trace of an electropherogram of a continuous-field electrophoresis experiment on a mixture of oligosaccharides. This trace includes data for Example 1, and the process by which it was obtained does not fall within the present invention.

The detector trace is shown in FIG. 1. While separate peaks in the electropherogram may be attributable to differences in shape between the molecules which may be due in part to branching, there is a notable lack of the expected polydispersity.

Figure 2A:
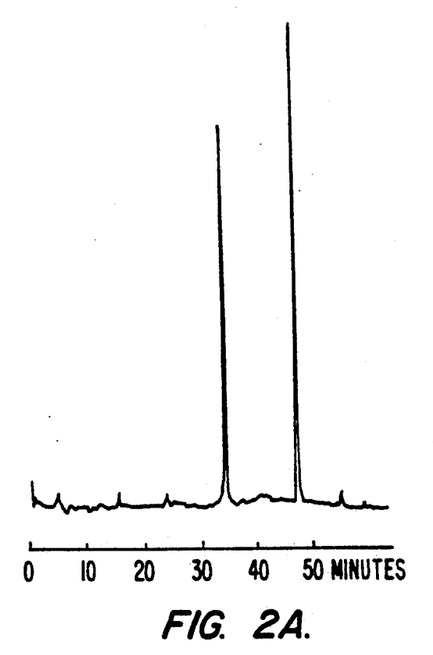
FIGS. 2A, 2B, and 2C are detector traces of electropherograms of individual standard polydextranes, also referred to in Example 1, and also not within the present invention.
Figure 2B:
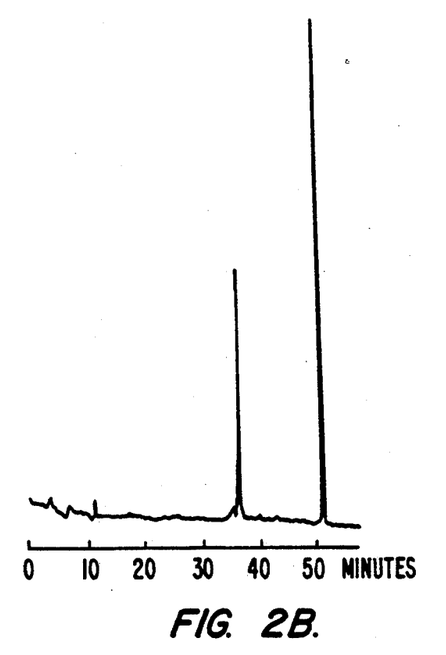
Figure 2C:
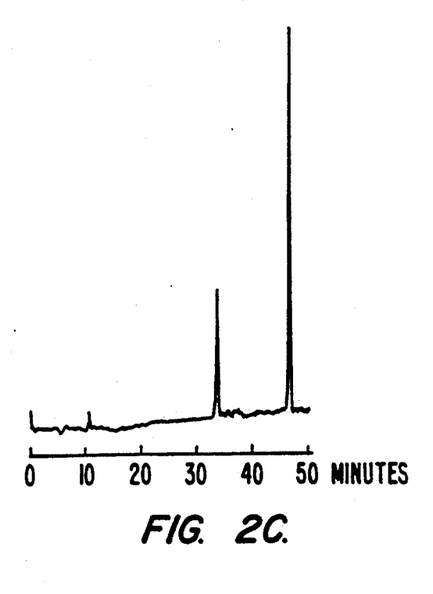

Attempts to assign approximate molecular weights to the peaks through comparison with standard commercial polydextranes confirmed the absence of the expected separation. The standard polydextranes were those of molecular weights 48,600, 273,000, and 667,800. The standards were individually run through a capillary electrophoresis procedure, using a capillary similar to that used for FIG. 1 except with an effective length of 21 cm (total length 31.5 cm), with the same 18% Instacryl solution and with a buffer of 50 mM Tris-borate (pH 8.7, basic treatment with ammonium hydroxide), sample loading having been achieved by electromigration injection over 20 seconds at 5 kV, and the electrophoresis having been conducted with an applied voltage of 20 kV (4 µA). The detector traces are shown in FIGS. 2A, 2B and 2C. These traces show that regardless of the vast differences in mass between these three standards, each one yielded two peaks with approximately the same migration times. It is speculated that the faster zone in each case contains the strictly linear molecule, while the slower zone contains molecules whose molecular shape is a departure from the usual due to branching.

EXAMPLE 2

This example illustrates the use and effect of the pulsed-field technique of the present invention on two mixtures of standard polydextranes. The first mixture included standards with molecular weights of 39,000, 70,000, 503,000 and 2,000,000, and the second mixture included standards with molecular weights of 8,800, 39,000, 70,000, 503,000, 607,800, and 2,000,000.

The capillary used in this experiment had an effective length of 20 cm (total length 29 cm) and was filled with 5% linear polyacrylamide. The buffer used was 50 mM Trisborate, 1 mM ethylenediaminetetraacetic acid, pH 8.2. Sample loading was achieved by electromigration injection for 20 sec at 2 kV, and electrophoresis was conducted with an alternating applied voltage of +/−10 kV (+/−340 V/cm) (the same field intensity alternating between opposite directions), using a rectangular wave form with a frequency of 3 Hz.

Figure 3:
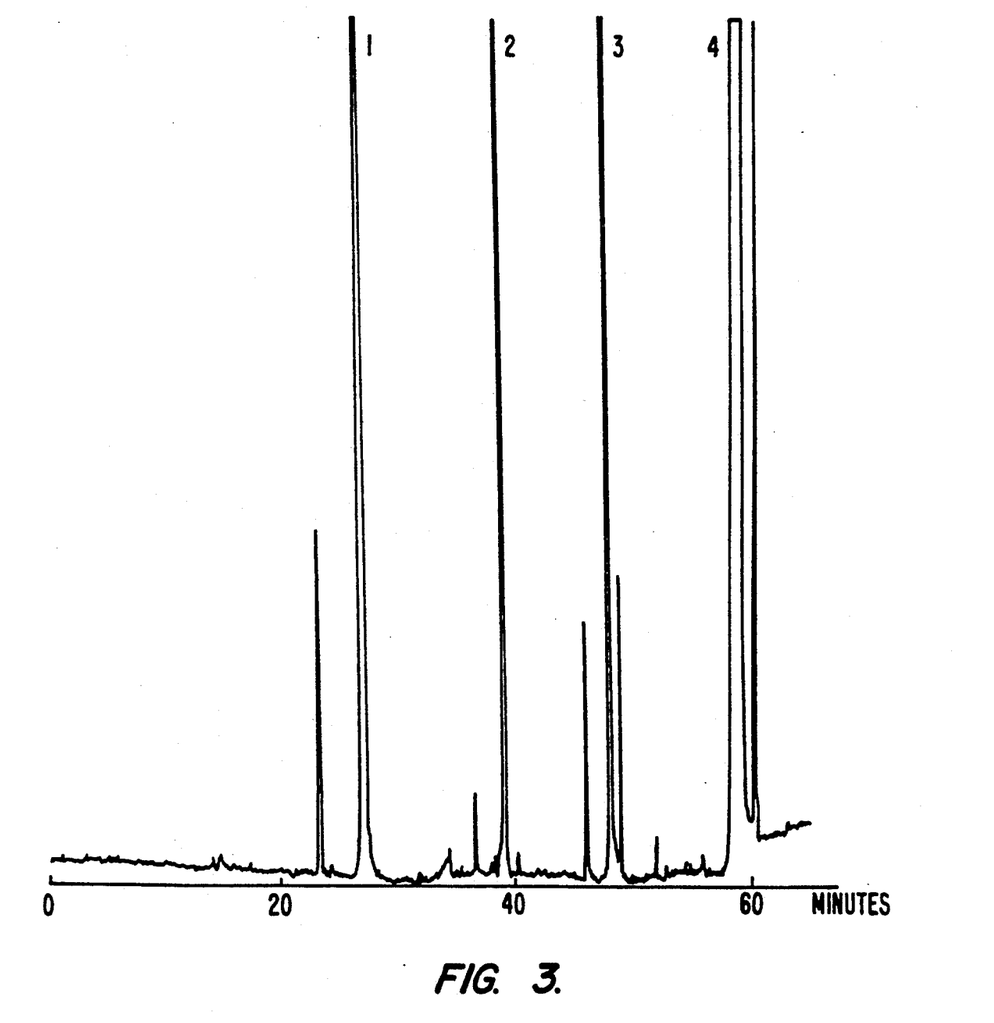
FIG. 3 is a detector trace of an electropherogram of a pulsed-field electrophoresis experiment reported in Example 2. The process used to obtain this trace is within the scope of the present invention.
Figure 4:
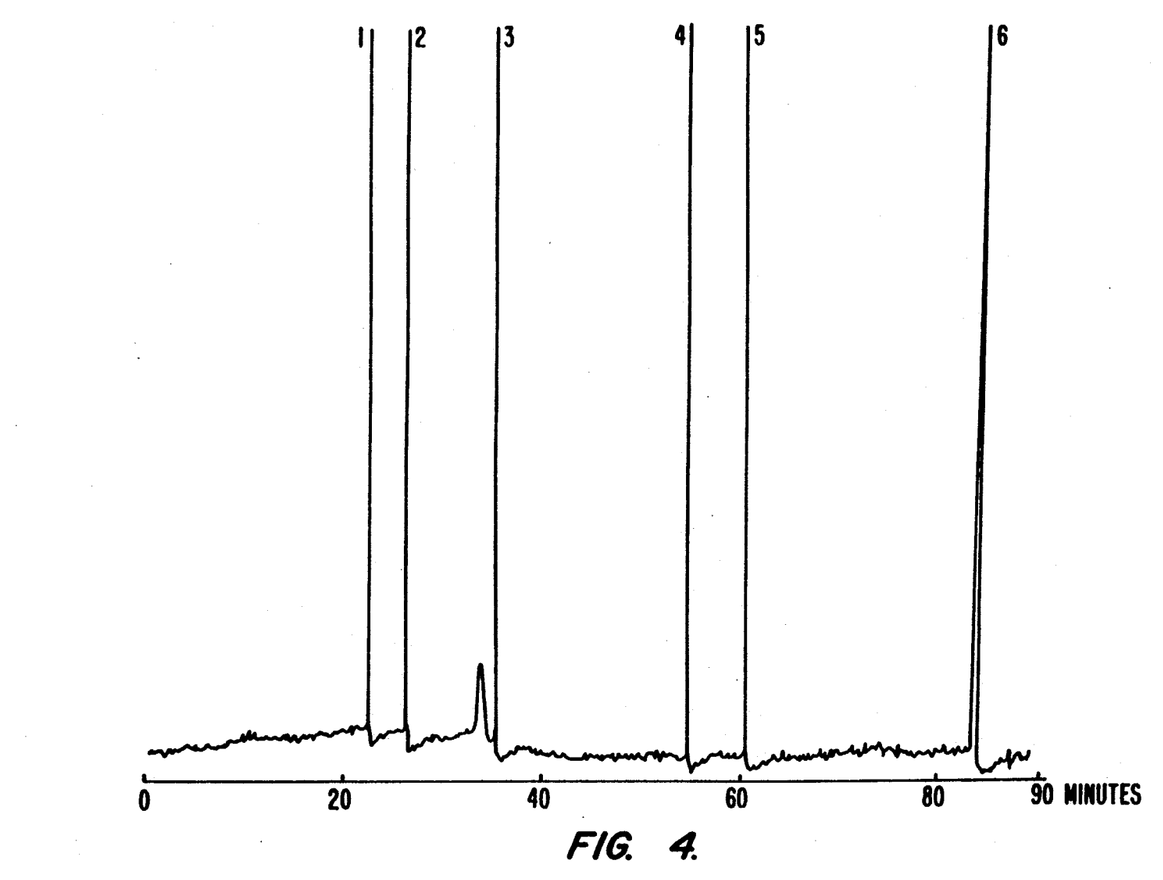
FIG. 4 is a detector trace of a further electropherogram of a pulsed-field electrophoresis experiment, also reported in Example 2 and likewise within the scope of the present invention.

The first experiment was performed on a mixture of polydextrane standards with molecular weights of 39,000, 70,000, 503,000 and 2,000,000. The forward-to-reverse time ratio of the pulses used was 3:1, and the detector trace for this experiment is shown in FIG. 3. The second experiment was performed on a mixture of polydextrane standards with molecular weights of 8,800, 39,000, 70,000, 503,000, 607,800, and 2,000,000. The forward-to-reverse rime ratio of the pulses for the second experiment was 2:1, and the detector trace is shown in FIG. 4.

The peaks in each trace were identified by comparison with traces of the individual polysaccharides obtained under the same conditions, and are numbered on the traces to correspond to the molecular weights of the standards when listed in order of increasing molecular weight. Each trace indicates a clear and clean separation of the standards, with the elution order corresponding directly to the molecular weight.

Figure 5:
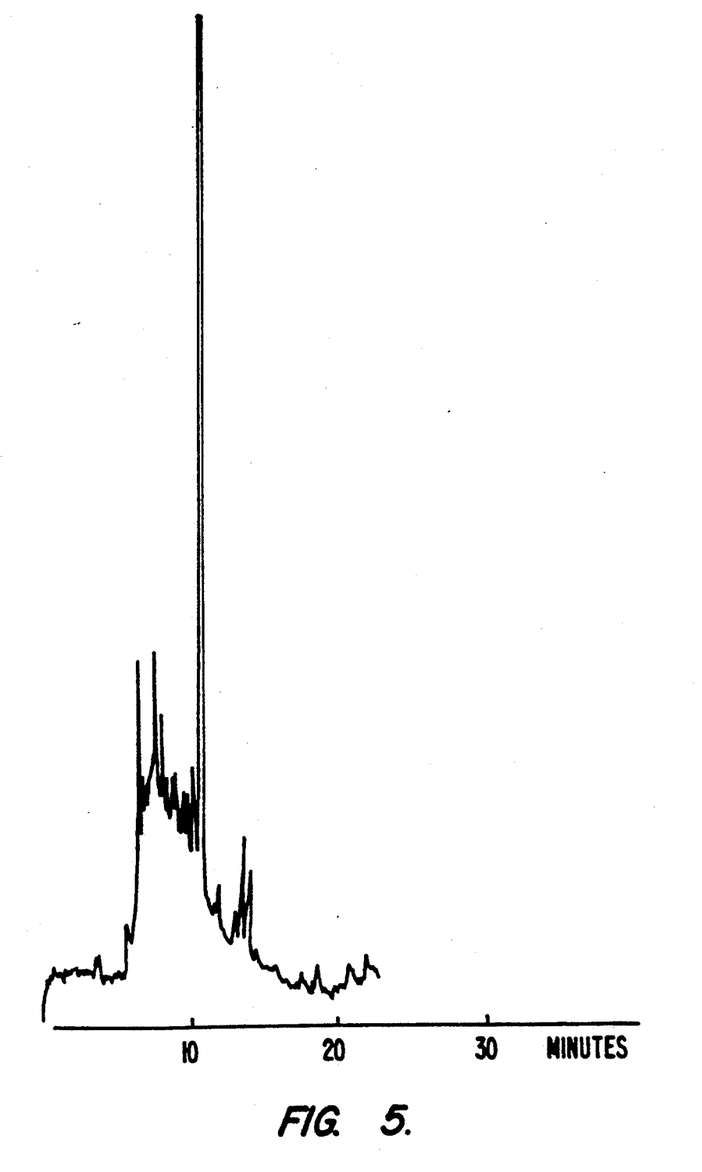
FIG. 5 is a detector trace of a still further electropherogram of a pulsed-field experiment reported in Example 2 and within the scope of the present invention.

To investigate whether polydispersity can be observed by the pulsed-field technique, the polydextrane standard of molecular weight 39,100 was run by itself through a capillary. The capillary had an effective length of 15 cm (total length 24 cm) and was filled with 4% linear polyacrylamide. All conditions used were the same as those used in the mixture represented by FIG. 3. The result is shown in FIG. 5, demonstrating that polydispersity can indeed be observed.

The foregoing is offered primarily for purposes of illustration. It will be readily apparent to those skilled in the art that the operating conditions, materials, arrangements of the system components and other system parameters described herein may be further modified or substituted in various ways without departing from the spirit and scope of the invention.

What is claimed is:

1. A method for the separation of a mixture of polysaccharides in a sample, comprising:
   (a) drawing said sample into a capillary through one end thereof defined as a sample introduction end, said capillary filled with an electrophoretic separation medium; and
   (b) imposing through said capillary an electric field in the direction away from said sample introduction end, said direction being defined as the forward direction, for time intervals defined as forward field time intervals, separated by intervening time intervals during which no electric field is imposed in said forward direction, the field strength of said electric field and the duration of said forward field and intervening time intervals being selected to cause electrophoretic migration of individual polysaccharides through said capillary in said forward direction at differing rates corresponding to the molecular weights of said polysaccharides.

2. A method in accordance with claim 1 in which said field strength is from about 30 V/cm to about 3,000 V/cm.

3. A method in accordance with claim 1 in which said field strength is from about 100 V/cm to about 1,000 V/cm.

4. A method in accordance with claim 1 in which said forward field time intervals alternate with said intervening time intervals at a frequency of from about 0.03 Hz to about 300 Hz.

5. A method in accordance with claim 1 in which said forward field time intervals alternate with said intervening time intervals at a frequency of from about 0.1 Hz to about 100 Hz.

6. A method in accordance with claim 1 in which said electrophoretic separation medium is a member selected from the group consisting of gels and polymer solutions.

7. A method in accordance with claim 1 in which said separation medium is a member selected from the group consisting of polacrylamide, polyethylene glycol, galactomannan and derivatives of cellulose.

8. A method in accordance with claim 1 in which said separation medium is linear polacrylamide.

9. A method in accordance with claim 1 in which said capillary has an internal diameter of from about 5 microns to about 300 microns.

10. A method in accordance with claim 1 in which said capillary has an internal diameter of from about 20 microns to about 100 microns.

11. A method in accordance with claim 1 in which said electric field is defined as a forward field, and an electric field in the opposite direction and defined as a reverse field is imposed through said capillary during said intervening time intervals.

12. A method in accordance with claim 11 in which said forward field is of a greater field strength than said reverse field.

13. A method in accordance with claim 11 in which each forward field time interval is of greater duration than the intervening time intervals immediately preceding and succeeding said forward field time interval.

14. A method in accordance with claim 11 in which said forward and reverse fields are of substantially equal field strength, and each forward field time interval is of greater duration than the intervening time intervals immediately preceding and succeeding said forward field time interval.

15. A method in accordance with claim 1 in which said forward field time intervals are of equal duration, and said intervening time intervals are of equal duration.

16. A method in accordance with claim 11 in which said forward field time intervals are of equal duration, and said intervening time intervals are of equal duration.

17. A method in accordance with claim 16 in which said forward field time intervals exceed said intervening time intervals in duration.

18. A method in accordance with claim 16 in which said forward and reverse fields are of substantially equal field strength, and said forward field time intervals exceed said intervening time intervals in duration.

19. A method in accordance with claim 11 in which said field strengths of said forward and reverse fields are independently from about 100 V/cm to about 1,000 V/cm.

20. A method in accordance with claim 11 in which said forward field time intervals alternate with said intervening time intervals at a frequency of from about 0.1 Hz to about 100 Hz.

* * * * *